United States Patent [19]

Androphy et al.

[11] Patent Number: 5,674,835

[45] Date of Patent: Oct. 7, 1997

[54] PAPILLOMAVIRAL EXPRESSION INHIBITORS

[75] Inventors: Elliot J. Androphy, Natick, Mass.; Douglas R. Lowy, Washington, D.C.; John T. Schiller, Silver Springs, Md.

[73] Assignees: New England Medical Center Hospitals, Inc., Boston, Mass.; The United States of America as represented by the Department of Health and Human Services, Washington, D.C.

[21] Appl. No.: 471,484

[22] Filed: Jun. 6, 1995

Related U.S. Application Data

[62] Division of Ser. No. 83,771, Aug. 7, 1987.

[51] Int. Cl.$^6$ .......................... A61K 38/00; A61K 31/70; C12N 7/00
[52] U.S. Cl. .................. 514/2; 514/44; 435/235.1
[58] Field of Search .................... 435/235.1; 514/2, 514/44

[56] References Cited

U.S. PATENT DOCUMENTS 4,775,630  10/1988  Tibbetts et al. .................. 435/320.1

OTHER PUBLICATIONS

Ahola et al., Nucleic Acids Res., vol. 11, No. 9, pp. 2639–2650 (1983).
Androphy et al., "Bovine papillomavirus E2 trans-activating gene product binds to specific sites in papillomavirus DNA," Nature 325:70–73 (1987).
Calabretta, B., Cancer Res., vol. 51, pp. 4505–4510 (1991).
Chen et al., "The primary structure and genetic organization of the bovine papillomavirus type 1 genome." Nature 299:529–534 (1982).
Goodarzi, G. et al., Biol. Abstr., vol. 94, pp. AB–239, Abstract 2262 (1991).
Hill et al., Appl. Environ. Microbiol., vol. 50, No. 5, pp. 1187–1191 (1985).
Lambert et al., "A Transcriptional Repressor Encoded by BPV–1 Shares a Common Carboxy–Terminal Domain with the E2 Transactivator," Cell 50:69–78 (1987).
Lusky et al., "Characterization of the Bovine Papilloma Virus Plasmid Maintenance Seqeuences," Cell 36:391–401 (1984).
Moskaluk et al., "The E2 'gene' of bovine papillomavirus encodes an enhancer–binding protein," Proc. Nat. Acad. Sci. USA 84:1215–1218 (1987).
Olson, C., In: The Papovaviridae, vol. 2, ed. N. Salzman et al., Plenum Press, NY, pp. 39–66 (1987).
Peterson et al., J. Infect. Diseases, vol. 153, No. 4, pp. 757–762 (1986).
Varley et al., Nucleic Acids Res., vol. 12, No. 17, pp. 6727–6739 (1984).
Spalholz et al., J. Virology, vol. 61, No. 7, pp. 2128–2137 (1987).
Spalholz et al., "Transactivation of a Bovine Papilloma Virus Transcriptional Regulatory Element by the E2 Gene Product," Cell 42:183–191 (1985).
Stenlund et al., "Messenger RNAs from the Transforming Region of Bovine Papilloma Virus Type I," J. Mol. Biol. 185:541–554 (1985).
Tidd, D.M., Anticancer Res., vol. 10, pp. 1169–1182 (1990).

Primary Examiner—Douglas W. Robinson
Assistant Examiner—Thanda Wai
Attorney, Agent, or Firm—Fish & Richardson P.C.

[57] ABSTRACT

A method of inhibiting the growth of a virus, the DNA of the virus including the nucleic acid sequence 5' ACCXNNNPyCGGTXY3', wherein each N, X, and Y is, independently, any nucleotide, and Py is C or T, the nucleic acid sequence being capable of binding to a protein encoded by the DNA of the virus, the protein, upon binding to the nucleic acid sequence, being capable of causing the enhancement of the transcription of DNA of the virus, the method including inhibiting the protein from binding to the nucleic acid sequence to repress the transcription of DNA of said virus to inhibit the growth of the virus.

11 Claims, 4 Drawing Sheets

FIGURE 3

| VIRUS | LOCATION | NUCLEOTIDES | SEQUENCE |
|-------|----------|-------------|----------|
| BPV1 | URR I | 7375-7362 | ACCG CCG CCGGTGC |
| BPV1 | URR IIa | 7620-7633 | ACCG CCA TCGGTGC |
| BPV1 | URR IIb | 7645-7632 | ACCT ATA TCGGTGC |
| BPV1 | URR IIIa | 7760-7772 | ACCG TTG CCGGTCG |
| BPV1 | URR IIIB | 7780-7793 | ACCG TCT TCGGTGC |
| BPV1 | URR IV | 7906-7893 | ACCG GTT TCGGTCA |
| BPV1 | E2 | 3088-3101 | ACCA TGG CCGGTGC |
| HPV16 | URR Ia | 35-48 | ACCG AAA TCGGTTG |
| HPV16 | URR Ib | 46-33 | ACCG ATT TCGGTTA |

PAPILLOMAVIRAL EXPRESSION INHIBITORS

This is a divisional of copending application Ser. No. 07/083,771, filed Aug. 7, 1987.

BACKGROUND OF THE INVENTION

This invention relates to DNA viruses.

Papillomaviruses are a group of small DNA viruses that cause warts and other diseases in humans and other animals. One type of papillomavirus is the bovine papillomavirus (BPV).

The upstream regulatory region (URR) that immediately precedes the early genes of BPV contains important cis-acting regulatory signals, including an origin of DNA replication (Lusky et al., 36 Cell 391 (1984)) and several promoters that function in early gene transcription (Stenlund et al., 182 J. Mol. Bio. 541 (1985)). Recent studies have shown that the URR also contains an enhancer element that can activate transcription of these promoters and of heterologous promoters in a manner that is independent of the enhancer's position and orientation relative to the promoter it activates. This enhancer is conditional in that it stimulates transcription when it is activated by a gene product of the BPV E2 open reading frame (ORF) Spalholz et al., 42 Cell 183 (1985)).

SUMMARY OF THE INVENTION

In general, the invention features, in one aspect, a method of inhibiting the growth of a virus whose DNA includes the nucleic acid sequence 5'ACCXNNNPyCGGTXY3' (the E2 binding site), wherein each N, X, and Y is, independently, any nucleotide, and Py is C or T. The nucleic acid sequence is specifically bound by a protein (the E2 protein) encoded by the DNA of the virus. The protein, upon binding to the nucleic acid sequence, causes the enhancement of the transcription of DNA of the virus. The expression, replication, and growth of the virus is inhibited by preventing the E2 protein from binding to the nucleic acid sequence (e.g., by introducing a substance that blocks the binding) and preventing E2 protein mediated enhancement of transcription.

In some preferred embodiments, the method includes contacting the viral DNA with a nucleic acid of at least 14 base pairs (and preferably less than 200 base pairs) that has a 14 base pair region of at least 80 percent homology (excluding N, Py, X, or Y) with the above nucleic acid sequence; the nucleic acid binds to the protein and thereby prevents the protein from binding to the nucleic acid sequence.

In other preferred embodiments, the method includes contacting the viral DNA with a blocking protein that binds to the nucleic acid sequence but does not enhance the transcription of the DNA of the virus, thereby prevent the E2 protein encoded by the DNA of the virus and synthesized in the papillomavirus infected cell from binding to the nucleic acid sequence (i.e., the E2 binding site). Preferably the protein includes an amino acid sequence that is substantially similar to the amino acid sequence that includes the DNA binding domain of an E2 protein. Substantially similar, as used herein, means that the sequences are at least 80% (more preferably at least 90%) homologous.

In other preferred embodiments, the virus is a papillomavirus (e.g. a human papillomavirus), and the protein is an E2 protein.

The invention features, in another aspect, an oligonucleotide consisting of between 14 and 200 base pairs and one strand of which contains the sequence 5'ACCXNNNPyCGGTXY3', wherein each N, X, and Y is, independently, any nucleotide, and Py is C or T; or 3'TGGVNNNPuGCCAVW5', wherein each N, V, and W is, independently, any nucleotide, and Pu is G or A.

The invention provides a simple way to treat warts in humans and a variety of diseases in other animals with compounds that are inexpensive and easy to make. The E2 binding site is present in all known papillomaviruses, and thus any disease caused by a papillomavirus can be treated according to the methods of the invention. Moreover, because the protein-enhancer interaction that the compounds block is specific to the viruses being treated, the compounds should not adversely affect cells that are not infected with a papillomavirus.

Other features and advantages of the invention will be apparent from the following description of the preferred embodiments and from the claims.

DESCRIPTION OF THE PREFERRED EMBODIMENTS

The drawings will first briefly be described.

BRIEF DESCRIPTION OF THE DRAWINGS

FIG. 1 is a diagrammatic representation of the BPV-1 genome and of the vector pCOE2-1.

FIG. 3 are DNA sequences that are bound by the E2 protein of BPV-1.

METHOD

The E2 binding sequence 5'ACCXNNNPyCGGTXY3', where X, N, and Y are as described above in the Summary of the Invention, is found in all known papillomaviruses. Each type of papillomavirus, e.g., BPV-1, H(human)PV-1, HPV-5, etc., contains a gene (the E2 gone) that encodes a protein (the E2 protein) that binds to the E2 binding sequence and acts as the transactivating protein of the E2 enhancer. E2 proteins of the various strains of papillomaviruses have closely homologous amino acid sequences.

Figure 1A:
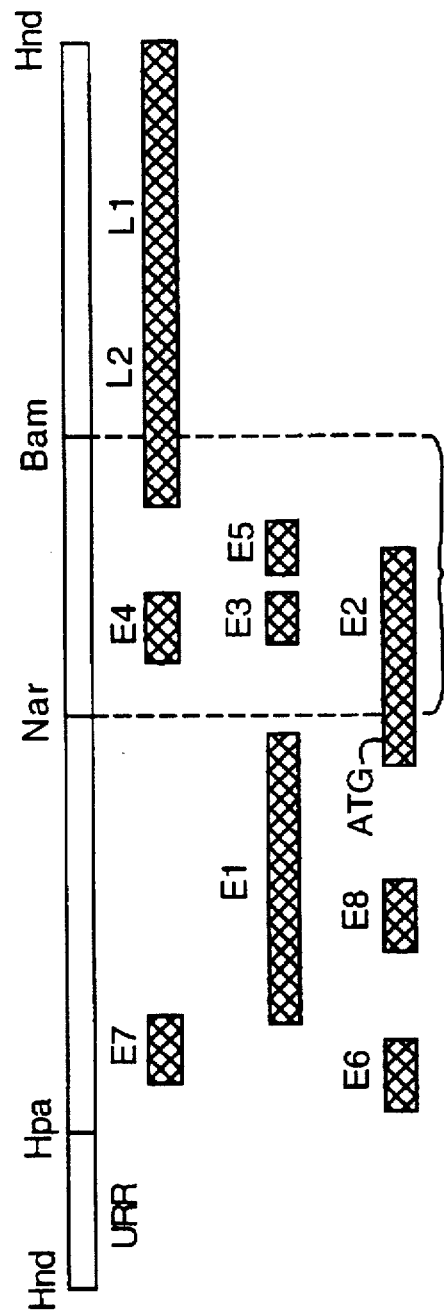
FIG. 1A. is a map of a papilloma virus genome, including the NarI-BamHI fragment of the BPV-1 virus.

Referring to FIG. 1A, an example of a papillomavirus genome, the 8 kb BPV-1 genome (linearized at the HindIII site), is depicted in nucleotide coordinates, with the HpaI site being at nucleotide 1. El-8 are the "early region" (expressed in cultured cells) open reading frames (ORF). URR is the upstream regulatory region.

The E2 binding site (or sequence) is located at several places in the URR and at other sites in the genome of BPV-1 and other papillomaviruses. E2 proteins bind to the binding sites and enhance the transcription of DNA. Inhibition of this binding represses the transcription of the DNA and thus inhibits viral growth.

There are two preferred methods of inhibiting the binding of an E2 protein.

In the first preferred method, a nucleic acid that includes the DNA sequence of the E2 binding site is transferred into cells containing the viral DNA. The nucleic acid binds to the E2 protein that is present in the papillomavirus infected cell, and thus prevents the protein from binding to the nucleic acid sequence in the viral genome.

In the second preferred method, a protein that is capable of binding to the above nucleic acid sequence but which does not enhance transcription is introduced into the cells. The protein binds to the sequence, thus preventing the E2 protein encoded by the viral DNA from binding and, accordingly, preventing the enhancement of transcription.

The structure, method of production, and characterization of E2 proteins, E2 protein-binding nucleic acids, and proteins capable of binding to nucleic acid sequences in the E2 DNA binding site without enhancing transcription are described next.

E2 Proteins

The E2 gene has been identified in the genomes of a variety of papillomaviruses, including in human strains such as HPV-1, HPV-5, HPV-6, HPV-8, HPV-16, HPV-18, and HPV-31. The DNA sequences of many of these papillomaviruses are readily accessible, e.g., in GenBank; the DNA sequence for BPV-1 is described in Chen et al., 7 Nature 529 (1982). Where the DNA sequence of an E2 gene is known, the structure of the E2 protein encoded can be readily identified, and the protein, or portion thereof, can be synthesized by standard methods.

The E2 protein of a particular papillomavirus whose DNA is not sequenced can also be readily obtained by those skilled in the art. In general, the DNA of a particular papillomavirus is fragmented, and a standard Southern Blot performed to find the fragment that is homologous to the below described E2 gene segment of BPV-1 (or any other appropriate papillomavirus E2 gene segment). If the fragment that binds to the BPV-1 E2 gene segment is large, e.g., 2000 base pairs, the fragment can be further digested with restriction enzymes until a smaller fragment is isolated with the appropriate homology. The fragments are subcloned into an expression vector, and the clones are screened to determine which ones produce a protein that binds to the E2 binding sequence (see below).

A segment of the E2 protein of BPV-1 that contains the DNA binding domain was produced and characterized as follows.

Figure 1B:
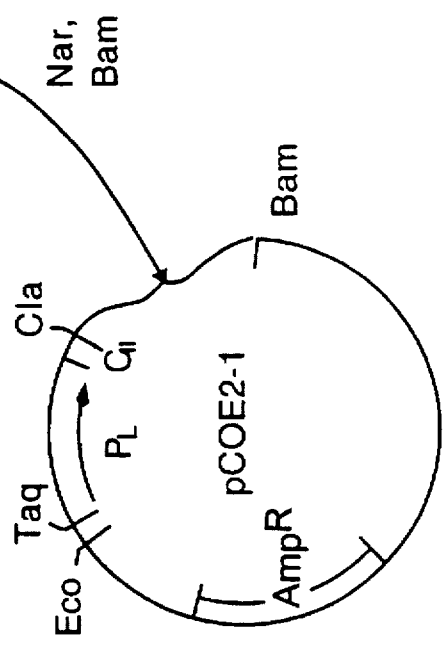
FIG. 1B is a restriction map of the vector PCOE2-1.
Figure 1C:
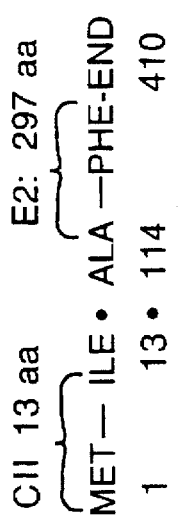
FIG. 1C is a diagram showing the orgin of amino acids in the cII-E2 fusion protein encoded by PCOE2-1.

Referring to FIG. 1, the 3'three-fourths of the BPV-1 E2ORF was cloned into pCO-5, an expression vector that contains the phage lambda $P_L$ promoter, and fused to the amino terminal end of the lambda cII protein, as described by Androphy et al., 230 Science 442 (1985). The NarI to BamHI fragment (nucleotides (nt) 2944–4450) of BPV-1 was inserted into the ClaI/BamHI site of pCO-5, fusing the $P_L$ promoter, a ribosome binding site, and 13 amino acids of the phage cII N-terminus to the E2 protein segment encoding DNA. The resulting vector, pCOE2-1, directs the synthesis of 13 N-terminal amino acids of cII followed in-frame by the 297 carboxy terminal amino acids of the BPV-1 E2 protein (the first in-frame stop codon is at nt 3838).

The above clone was introduced into an E. coli strain N6405 (230 Science 442; many other well-known strains can also be used) that contains the lambda $cI^{857}$ts repressor of $P_L$. The bacteria were grown in minimal medium at 32° C., induced at 42° for 15 minutes, and labeled with $^{35}$S-methionine for 15 minutes. After sequential treatment of the bacteria with lysozyme and DNAase I, proteins were solubilized with 4M urea/1 mM dithiothreitol (DTT). At this point, approximately two percent of total bacterial protein is the 37 kilodalton (kDa) E2 fusion protein segment.

In order to produce antibodies to the E2 protein segment, the 37 kDa band was extracted from SDS-polyacrylamide gels and used with Freund's adjuvant to immunize rabbits at 3- to 4-week intervals. This resulted in rabbit sera with antibodies that recognized the E2 fusion protein segment but did not cross-react with bacterially synthesized BPV E6 or H-ras fusion proteins that had the same cII amino-terminus. This result indicates that the sera recognized E2 specific epitopes and not the cII portion of the protein.

A band of the same molecular weight was also immunoprecipitated with antisera raised against an in vitro synthesized peptide derived from the predicted BPV-1 E2 protein sequence, confirming that the 37 kDa band was a BPV-1 E2 fusion protein segment.

E2 protein-binding DNA

To test the ability of an E2 protein to specifically bind to a papillomavirus' DNA, a stringent DNA immunoprecipitation assay was used (145 J. Mol. Biol. 471 (1981); Androphy et al., 325 Nature 70 (1987)). Labeled DNA fragments are first incubated With protein-antibody complexes linked to insoluble Sepharose beads in the presence of excess unlabeled competitor DNA. After washing the complexes several times to remove the unbound fragments, the bound fragments are disassociated and analyzed by gel electrophoresis.

The following is an example of the above described assay.

Fifty ng of the partially above purified BPV-1 E2 protein segment (50% by acrylamide gel analysis) was diluted with DIB (20 mM HEPES pH 7.2, 150 mM KCl, 0.05% NP 40, 1 mM EDTA, 1 mM DTT, 1% aprotinin) and incubated at 4° C. with E2 specific antisera. Complexes were collected with protein A-Sepharose and washed with DIB. After restriction endonuclease digestion and end-labeling with $^{32}$P-dNTPs using the Klenow fragment of DNA Polymerase I, 20 ng of DNA were added in 0.2 ml of DIB containing 400 ng of unlabeled pML2d (Lusky et al., 293 Nature 79 (1981)). After 1 hour at 37° C., the complexes were pelleted and washed 4 times with DIB, dissociated in 1% SDS at 65° C., phenol-chloroform extracted, and the released DNA ethanol precipitated after the addition of carrier DNA. The resuspended DNA was denatured and analyzed on standard acrylamide sequencing gels or on a gradient sequencing gel.

In the initial DNA binding experiment, the full length 8 kilobase (kb) BPV genome was digested with a combination of BamHI, HindIII, and Sau96I endonucleases and then end labeled with $^{32}$P. Two fragments were specifically bound by the BPV-1 E2 protein segment-antibody complexes. One fragment had 498 bp (nt 6958–7456), and the other had 233 bp (nt 7586–7816). Both fragments are within the segment of the URR that has enhancer activity. Specific binding occurred over a pH range of 6.8 to 7.4, a temperature range from 4° to 37° C., and in concentrations of the detergent NP40 from 0.05 to 0.5 percent. In control experiments, no DNA binding was detected when pre-immune sera was used in the assay or when the same cII peptide was linked to the BPV E6 protein or the H-ras protein and the assay performed with either the E2 antisera or antisera that recognize the E6 or H-ras peptides. Accordingly, the binding of the two fragments is due to a sequence specific interaction with the E2 fusion protein segment. The BPV E2 fusion protein segment also reacts specifically with the HPV16 URR (Seedorf et al., 145 Virology 181 (1985)), with binding to a single 88 bp fragment (nt 24–112). Neither the SV40 genome nor the Harvey murine sarcoma virus LTR, which both contain enhancers, possess sequences that are specifically recognized by the E2 protein segment in this assay, indicating that DNA sequences recognized by the peptide are not common to other enhancer elements.

When the BPV fragments are thermally denatured prior to incubation with the E2-antibody complexes, all of the single strand fragments above 100 nt are bound, indicating that the E2 protein segment binds to single stranded DNA nonspecifically.

Since other sequence specific DNA binding proteins may bind DNA nonspecifically when assayed under conditions of protein excess, the above experiments were performed with low concentrations of the E2 protein segment. When more of the E2 protein segment was used in the assay, two additional binding sites in the BPV-1 genome were revealed. One is in a 219 bp fragment that is located further upstream in the URR (nt 7819-93), and the other is in a 355 bp fragment located in the E2 ORF (nt 2904-3259). Thus, there are several E2 binding sites within the BPV genome, most are located within the URR, and there is a hierarchy in the affinities of these sites for the peptide. At least one additional binding site was also detected in the HPV16 genome when the concentration of E2 protein segment was increased.

Figure 2:
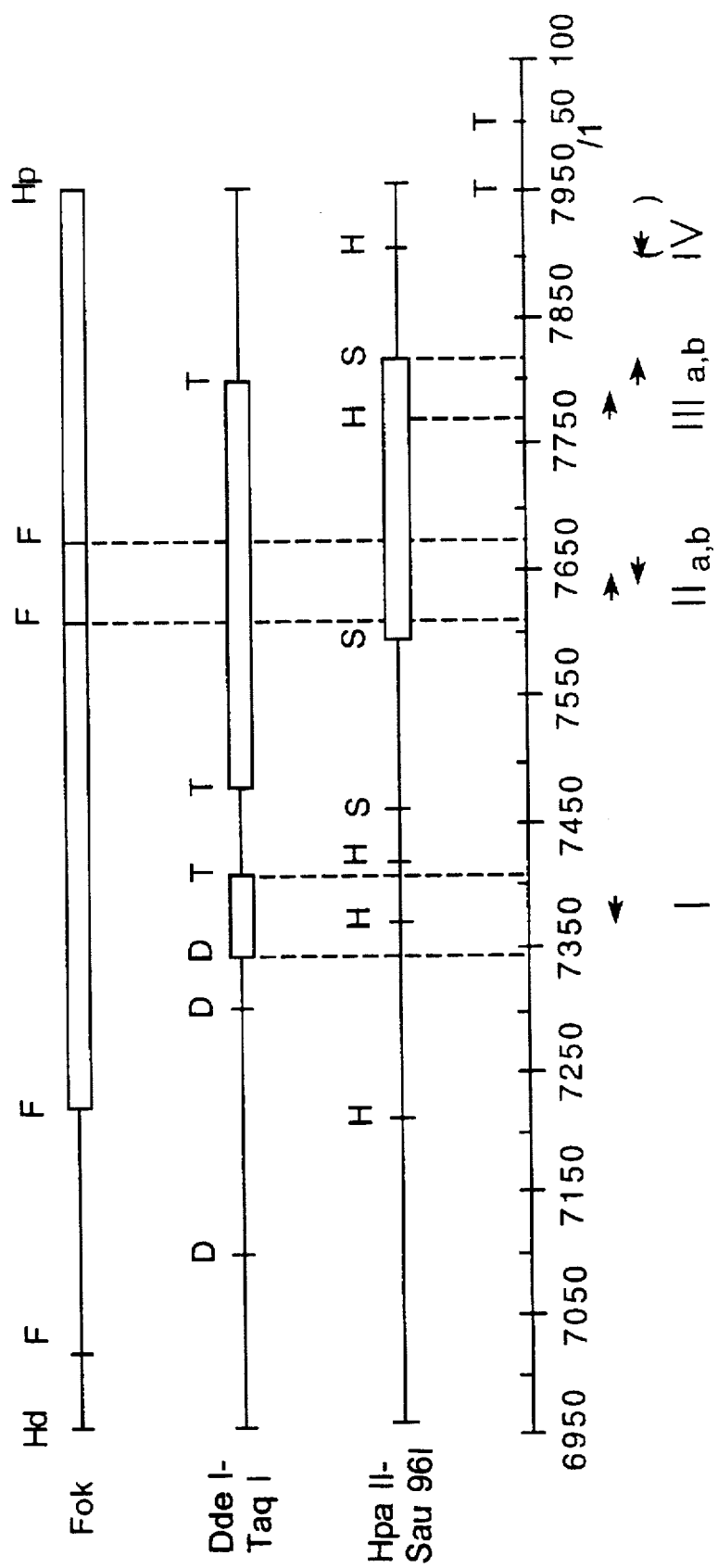
FIG. 2 is a restriction endonuclease map of the enhancer region of BPV-1.

In order to more precisely determine the number and location of the high affinity E2 binding sites, the 987 bp HindIII to HpaI (nt 6958-7945) URR fragment was isolated, and the ability of the E2 protein segment to recognize this segment after digestion with various restriction endonucleases was tested (FIG. 2). Three fragments of 395, 275, and 60 bp were immunoprecipitated after FokI digestion; DdeI and TaqI revealed two binding fragments of 317 and 70 bp; and digestion with HpaII and Sau96I generated two binding fragments of 179 and 56 base pairs. Since the 56, 60, and 70 bp fragments that were bound by the peptide are non-overlapping, the E2 protein segment recognizes at least three high affinity elements in the LFRR, located between nt 7366-7406, nt 7624-7683, and nt 7767-7822 (FIG. 2). The results also demonstrate the ability of the E2 complexes to specifically and efficiently bind small DNA fragments.

The DNA sequences of the fragments to which the peptide bound were compared to determine if they contain common sequences (FIG. 3). All of the fragments that specifically bound the E2 protein segment contain a similar motif which has the consensus sequence of 5'ACC(G)NNNPyCGGT (GC)3' (nucleotides in parentheses are preferred but not invariant; N can be any nucleotide, and Py can be C or T). This motif is found on either strand of the DNA, and in two instances two copies are in close proximity to each another (sites I-IV in FIG. 2). Site I is not bound in the HpaII-Sau96I digest and HpaII cleaves the putative E2 recognition sequence of this site segments. Sequence analysis of BPV and HPV16 indicated that the motif is limited to those segments that are recognized by the E2 protein segment. Sequences similar to this motif have been reported in the URRs of all other papillomaviruses that have been sequenced (Dartman et al., 151 Virology 124 (1986)). The sequences are not, however, present in the other viral genomes surveyed in a computer search, including SV40, Polyoma, Bovine leukemia virus, and Moloney murine leukemia virus.

Inhibition of E2 Protein Binding

The ability of a 23 bp URR fragment that includes the consensus sequence to inhibit the specific binding of the BPV-1 E2 protein segment to BPV DNA was examined in a competitive inhibition assay. The ability of a 23 bp URR fragment that does not contain the consensus sequence to inhibit the binding also was examined.

Assays were performed using 25 mg of the BPV-1 E2 protein segment in the DNA precipitation procedure described above, except that 1-1000 ng of competing unlabeled fragment was added to the labeled BPV DNA prior to its incubation with the antibody-E2 complexes. The competing double-stranded DNA fragment contained either the sequence 5'CGTCAAACCGTCTTCGGTGCTC3' (the E2 binding site sequence IIIb is underlined), or 5'GCGCAT-AATCAGCTTAATTGGTG3' (no E2 binding site sequence).

The fragment that includes the E2 binding site sequence effectively blocked the immunoprecipitation of the BPV fragments; it was approximately one thousand times more effective than the 23 bp fragment not containing the consensus sequence.

Single stranded oligonucleotides containing the sequences did not block the immunoprecipitation of the double stranded BPV DNA fragments.

E2 Specific DNA Binding Activity in BPV Transformed Cells

Protein fractions from isolated nuclei of BPV transformed C127 cells (ID14) and control C127 cells were tested for the presence of specific DNA binding activity that could be immunoprecipitated by the E2 antisera in the DNA immunoprecipitation assay as described above. The 233 bp Sau96I BPV URR fragment, which contains four of the binding motifs, was specifically bound and immunoprecipitated with the ID14 extract but not with the C127 extract. The DNA fragment was immunoprecipitated by the anti-E2 sera but not by the preimmune sera, indicating that the binding protein has E2 specific epitopes.

The immunoprecipitation of the 233 bp fragment was competively blocked by the 23 bp fragment that contained the E2 binding site sequence but not by the fragment that lacked a sequence, indicating that the BPV transformed cells synthesize an E2 protein and that the E2 protein in BPV transformed cells has the same DNA binding specificity as that of the bacterially synthesized E2 protein.

Protein Binding to E2 Binding Site Sequence

Figure 4:
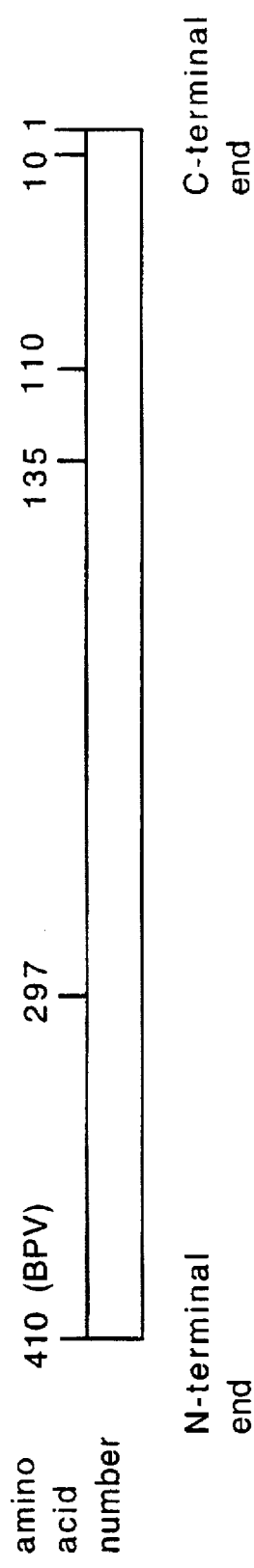
FIG. 4 is a diagrammatic representation of E2 proteins.

Referring to FIG. 4, the DNA binding domain of E2 proteins, i.e., the portion of the protein responsible for the DNA binding activity, is located in the 135 amino acids that comprise the C-terminal segment of the molecules (amino acid 1 being the carboxy terminal amino acid). In particular, the DNA binding domain is substantially located between amino acids 10 and 110. The transcription enhancement activity domain of E2 proteins is at least in part located in the N-terminal segment (the segment between amino acid 297 and the N-terminal amino acid) of the molecules.

Introducing into a papillomavirus infected cell a protein that contains the DNA binding domain of an E2 protein, but which does not include the transcription enhancement domain, blocks E2 protein binding sites without enhancing the transcription of viral DNA. Suitable blocking proteins include (a) those segments of E2 proteins consisting of the DNA binding domain; (b) segment (a) plus some or all of the remainder of amino acids 1-110,or 10-110, of the C-terminal segment; (c) segments (a) or (b) plus some or all of amino acids 110-297 of an E2 protein; (d) segment (c), plus all or some of the amino acids in the N-terminal segment of an E2 protein that are not responsible for transcription enhancement activity; and (e) any of the above segments having non-E2 protein amino acid sequences added to either the N or C-terminal end of the segment. Preferably, the protein does not contain more than 500 (more preferably 180, most preferably 135) amino acids.

The above segments can be readily synthesized using standard recombinant DNA techniques, or solid phase synthesis techniques.

To determine if a particular segment, e.g., one that consists of less than amino acids 10-110 of the C-terminal segment of an E2 protein, is suitable for use as a blocking protein, the segment is tested using the DNA binding assay described above. If the segment binds the E2 DNA binding sequence and does not contain any portion of the N-terminal segment of an E2 protein, it is suitable for use as a blocking protein without further screening because the fragment will not have transcription enhancement activity.

If the tested segment also contains part of the N-terminal segment of an E2 protein, the segment should be tested further, e.g., according to the general methods described in Spalholz et al., supra, to determine if the segment lacks transcription enhancement activity. For example, the DNA that encodes the tested segments is linked to a suitable promoter, e.g., SV40 or a retroviral LTR, and cotransfected into a suitable cell line (e.g., CV-1 cells) along with the E2 binding site linked to an indicator gene (e.g., CAT gene). The cell line will produce the segment being tested, and the segment will bind to the E2 binding site. If the segment includes the portion of the N-terminal E2 segment that is responsible for transcription enhancement activity, the CAT gene will be expressed, and the segment is not suitable for use as a blocking protein. If the segment lacks the portion of the N-terminal E2 segment that is responsible for the enhancement activity, the gene will not be expressed, and the segment is suitable for use as a blocking protein.

A specific example of a blocking protein is the BPV-1 E2 protein segment described above.

Use

An oligonucleotide having a DNA sequence within the above formula is able to bind to any papillomavirus E2 protein in vivo. Cells infected with a papillomavirus can be saturated with the oligonucleotide to bind the E2 protein produced by that papillomavirus and prevent the protein from interacting with viral DNA and enhancing viral gene expression, resulting in the inhibition of the expression of the virus.

The oligonucleotides can be provided in pharmaceutically acceptable media to be applied to regions infected by the papilloma virus, or for injection into an animal. They are especially useful for application to a human wart. The oligonucleotides must be at least 12–14 nucleotide bases in length; for external application, e.g., to a wart the oligonucleotides should not have more than about 200 base pairs (more preferably no more than 100 base pairs, most preferably no more than 50 base pairs), or the molecules will not penetrate the skin. The oligonucleotides may be either free in solution, or ligated to the DNA of a non-pathogenic virus for transfection into an infected cell. Alternatively, a small amount (e.g., about 0.1–10 µg) of an oligonucleotide preparation (e.g., the oligonucleotide dissolved in DMSO and/or saline) may be allowed to penetrate viral infected cells (e.g., by the method described in 82 P. Nat. Acad. Sci. 2781 (1986)) by applying the preparation to an infected region; preferably in the preparation contains EDTA to prevent nuclease activity.

Peptides containing a papillomavirus E2 protein's binding domain (but not the transcription enhancement domain) can also be used to inhibit the growth and expression of a papillomavirus. The peptide can be introduced into viral-infected cells so that it can bind to the E2 DNA binding sites and prevent native E2 protein from binding. A peptide containing the binding domain of any E2 protein can be used to treat any papillomavirus infection. The peptides can be dissolved in a pharmacologically acceptable buffer and applied to infected cells. DMSO and EDTA can be used to help the uptake of the peptide and to inhibit protease degradation. Alternatively, the peptide can be fused chemically, or by standard genetic engineering techniques, to a cell specific receptor peptide, e.g., epidermal growth factor, so that the peptide is more readily taken up by cells. Further, the peptide may also be fused to a nuclear targeting sequence (see 7 Mol. & Cell. Bio. 2451 (1987); 39 Cell 499 (1984); 46 Cell 575 (1986); 6 Mol. & Cell. Bio. 4136 (1986); 311 Nature 33 (1984)) so that the E2-protein fragment is transported to the cell nucleus where it can inhibit viral growth. Preferably, the peptides are applied in the range of 1–1,000 µg per kg animal, or at 1–1,000 µg/ml when used topically.

Other embodiments are within the following claims.

What is claimed is:

1. A method of inhibiting the growth of a papillomavirus whose DNA comprises the nucleic acid sequence 5'ACCXNNNPyCGGTXY3', wherein each N, X, and Y is, independently, any nucleotide, and Py is C or T, said nucleic acid sequence binding to a DNA binding domain within the C-terminal 135 amino acids of an E2 protein encoded by the DNA of said virus, said protein, upon binding to said nucleic acid sequence enhancing transcription of DNA of said virus, said method comprising applying a composition to a region of cells infected by the papilloma virus, said composition comprising a double-stranded nucleic acid fragment comprising the sequence 5'ACCXNNNPyCGGTXY 3', wherein each N, X, and Y is, independently, any nucleotide, and Py is C or T, said nucleic acid fragment binding to said protein and thereby inhibiting said protein from binding to said nucleic acid sequence in said virus.

2. The method of claim 1, wherein said nucleic acid fragment in said composition comprises 200 base pairs or fewer.

3. The method of claim 1, wherein X is C and Y is G.

4. The method of claim 1, wherein said virus is a human papillomavirus.

5. The method of claim 1, wherein said papilloma virus is a bovine papillomavirus.

6. The method of claim 1 further comprising applying said composition to the skin of a person infected with said papilloma virus.

7. A method of inhibiting the growth of a papillomavirus whose DNA comprises the nucleic acid sequence 5'ACCXNNNPyCGGTXY3', wherein each N, X, and Y is, independently, any nucleotide, and Py is C or T, said nucleic acid sequence binding to a DNA binding domain within the C-terminal 135 amino acids of an E2 protein encoded by the DNA of said virus, said protein, upon binding to said nucleic acid sequence enhancing transcription of DNA of said virus, said method comprising applying a composition to a region of cells infected by the papilloma virus, said composition comprising a blocking protein that binds to said nucleic acid sequence without causing an enhancement of said transcription, thereby preventing said protein encoded by the DNA of said virus from binding, wherein said DNA binding domain of said blocking protein is located within the C-terminal 135 amino acids of an E2 protein.

8. The method of claim 7, wherein said DNA binding domain is located within the 110 amino acids of the C-terminal end of an E2 protein.

9. The method of claim 7, wherein said DNA binding domain is located within amino acids 10–135 of the C-terminal end of an E2 protein, wherein amino acid 1 is the carboxy terminal amino acid.

10. The method of claim 7, wherein said DNA binding domain is located within amino acids 10–110 of the C-terminal end of an E2 protein, wherein amino acid 1 is the carboxy terminal amino acid.

11. The method of claim 7, further comprising applying said blocking protein to the skin of a person infected with said papilloma virus.

* * * * *